US005689020A

United States Patent [19]

Boyce

[11] Patent Number: 5,689,020
[45] Date of Patent: Nov. 18, 1997

[54] HIGH TEMPERATURE CHLORINATION PROCESS FOR THE PREPARATION OF POLYCHLOROOLEFINS

[75] Inventor: C. Bradford Boyce, Baton Rouge, La.

[73] Assignee: LaRoche Industries Inc., Atlanta, Ga.

[21] Appl. No.: 614,005

[22] Filed: Mar. 11, 1996

[51] Int. Cl.$^6$ ................................................ C07C 21/04
[52] U.S. Cl. .................................................. 570/216
[58] Field of Search ................................. 570/216, 226

[56] References Cited

PUBLICATIONS

CA 69: 86337 , 1967.
CA 69: 51544 , 1967.

*Primary Examiner*—Shean C. Wu
*Attorney, Agent, or Firm*—Richard J. Hammond

[57] ABSTRACT

A process is disclosed for preparing a compound selected from the group consisting of 1,1,3,3-tetrachloropropene and 1,3,3,3-tetrachloropropene. The process comprises a. admixing a hydrocarbon compound selected from the group consisting of propene, 1-chloropropene, 3-chloropropene, 1,1-dichloropropene, 1,3-dichloropropene, 3,3,-dichloropropene, 1,1-dichloropropane, 11,2-dichloropropane, 1,3-dichloropropane, 1,1,3-trichloropropene, 1,3,3-trichloropropene, 3,3,3-trichloropropene, and mixtures thereof with an inert diluent gas;

b. preheating said mixture to from about 300° C. to about 400° C. and then mixing it with chlorine gas; and c. thermally treating the mixture of step b. at a temperature of from about 400° C. to about 600° C.

The desired tetrachloropropene is then separated.

10 Claims, No Drawings

HIGH TEMPERATURE CHLORINATION PROCESS FOR THE PREPARATION OF POLYCHLOROOLEFINS

FIELD OF INVENTION

This process relates to a process for the preparation of 1,1,3,3-tetrachloropropene and 1,3,3,3-tetrachloropropene by the high temperature chlorination of propene, monochloropropenes, dichloropropenes and trichloropropenes where the chloropropenes have no chlorine on the number 2 carbon. The process may also utilize 1,2-dichloropropane.

BACKGROUND OF THE INVENTION

The need exists for an inexpensive source of 1,1,3,3-tetrachloropropene as the starting material for the manufacture of HFC-245fa (1,1,1,3,3-pentafluoropropane), a "third generation" CFC-11 ($CCl_3F$) replacement in the fluorocarbons industry. One way to obtain the desired tetrachloropropene is to eliminate the elements of HCl from 1,1,1,3,3-pentachloropropane by treatment with base or heating with a Lewis acid like ferric chloride, general methods well established in the art. The pentachloropropane can be prepared by the free radical coupling of carbon tetrachloride with vinyl chloride using a copper chloride/amine catalyst (Bull. Chem. Soc. Japan 43 1127 (1970) or an initiator such as benzoyl peroxide (Organic Reactions Vol 13 Chap. 3, 1963). These routes involve two chemical steps and significant processing problems. Carbon tetrachloride may also be coupled with acetylene using a free radical catalyst to yield 1,3,3,3-tetrachloropropene (U.S. Pat. No. 3,338,981 [1967]), which will spontaneously rearrange with acid, but the yield is poor. Even less commercially attractive routes to tetrachloropropene have been reported using 3,3-dichloroacrolein and acetyl chloride with aluminum trichloride catalyst (Bull. Soc. Chim. France 2147 (1963), 1,1,3-trichloropropene and potassium thioacetate or sodium sulfide followed by chlorine (French Pat. 1,496,124 and 1,496,180 [1966]), and the pyrolysis of 1,1,2,3-tetrachlorocyclopropane (Chem. Com. 1081 [1967]).

In a typical chlorination of olefinic hydrocarbons, chlorine is added across the double bond to produce dichloro-substituted hydrocarbons, i.e., propene gives good yields of 1,2-dichloropropane. However, the reaction of chlorine with propene is changed from addition to substitution by operating at 400° to 600° C. yielding allyl chloride with good selectivity. This reaction is the basis of the commercial manufacture of allyl chloride. The primary byproducts are 1- and 2-chloropropene, 1,3- and 3,3-dichloropropene, and 1,2-dichloropropane (Ind. Eng. Chem. 31[2] 1530 (1939)).

High temperature chlorination of 1- or 3-chloropropenes yield allylic substitution products 1,3- and 3,3-dichloropropenes. 1,1-, 1,3- and 3,3-dichloropropenes yield 1,1,3- and 1,3,3trichloropropenes with high selectivity (J.Am. Chem. Soc. 75 1392 (1953)).

High temperature chlorination of 1- or 3-chloropropenes yield allylic substitution products 1,3- and 3,3-dichloropropenes. 1,1-, 1,3- and 3,3-dichloropropenes yield 1,1,3- and 1,3,3-trichloropropenes with high selectivity (J.Am. Chem. Soc. 75 1392 (1953)).

It should be noted that U.S. Pat. No. 4,319,062 discloses that dichloropropenes are relatively stable to conditions that may thermally crack 1,2-dichloropropane. This latter compound produces predominately 1- and 3-monochloropropenes under high temperature cracking conditions.

DESCRIPTION OF THE PREFERRED EMBODIMENTS

In the process of the present invention, the starting materials are hydrocarbon compounds selected from the group consisting of propene, 1-chloropropene, 3-chloropropene, 1,1-dichloropropene, 1,3-dichloropropene, 3,3-dichloropropene, 1,1-dichloropropane, 1,2-dichloropropane, 1,3-dichloropropane, 1,1,3-trichloropropene, 1,3,3-dichloropropene, and 3,3,3-trichloropropene.

In carrying out the process of the present invention, one or more of the starting materials listed above is diluted with 3 to 4 molar equivalents of an inert diluent gas such as nitrogen or, preferably, carbon tetrachloride. This mixture is preheated to 300° to 400°, preferably 340° to 360° C. and passed into a reactor where it is mixed with about 110% of the theoretical amount of chlorine. Depending on the feed, the amount of chlorine may be adjusted up or down to maximize the yield of 1,1,3,3-tetrachloropropene. The reaction is exothermic. The mixture within the reactor is maintained between 400° and 600° C., preferably 480° to 520° C. The size of the reactor is chosen to provide a residence time of 0.1 to 10 seconds, preferably 2 to 5 seconds. The exit gases (which contain the desired product) are immediately quenched preferably with a water spray. The resulting aqueous HCl and organic layers are separated. The organic layer is stripped of solvent and low boiling substances and distilled to obtain the desired tetrachloropropene.

EXAMPLES

The reactor comprises a nickel tube 2 cm. I.D.×50 cm. surrounded by a tube furnace and maintained at a temperature of about 500° C. The temperature is measured by thermocouple within the reactor. The material to be chlorinated is pumped into an silicone oil heated evaporator at a rate of about 0.25 moles per minute. The resulting vapor is admixed with gaseous chlorine with the flow controlled by a mass flow controller. The reactants are mixed in a 0.2 cm. diameter jet attached directly to the reactor. After exiting the reactor, the reaction products are passed thru a water-cooled condenser and into a 500 ml flask. The chlorinated products are then isolated by conventional methods. The effluent, largely HCL vapor, is scrubbed with water.

I claim:

1. A process for preparing a compound selected from the group consisting of 1,1,3,3-tetrachloropropene and 1,3,3,3-tetrachloropropene by
   a. admixing a hydrocarbon compound selected from the group consisting of propene, 1-chloropropene, 3-chloropropene, 1,1-dichloropropene, 1,3-dichloropropene, 3,3,-dichloropropene, 1,1-dichloropropane, 1,2-dichloropropane, 1,3-dichloropropane, 1,1,3-trichloropropene, 1,3,3-trichloropropene, 3,3,3-trichloropropene, and mixtures thereof with an inert diluent gas;
   b. preheating said mixture to from about 300° C. to about 400° C. and then mixing it with chlorine gas; and
   c. thermally treating the mixture of step b. at a temperature of from about 400° C. to about 600° C.

2. The process according to claim 1 wherein said compound is 1,1,3,3-tetrachloropropene.

3. The process according to claim 2 wherein said hydrocarbon compound is mixed with a diluent prior to said thermal treatment.

4. The process according to claim 3 wherein from about three to about four moles of diluent per mole hydrocarbon compound is employed.

5. The process according to claim 1 wherein said thermal treatment is at a temperature of fro about 480° C. to about 520° C.

6. The process according to claim 1 wherein said compound is 1,3,3,3-tetrachloropropene.

7. The process according to claim 6 wherein said hydrocarbon compound is mixed with a diluent prior to said thermal treatment.

8. The process according to claim 7 wherein from about three to about four moles of diluent per mole hydrocarbon compound is employed.

9. The process according to claim 8 wherein said thermal treatment is at a temperature of from about 480° C. to about 520° C.

10. A process for preparing an olefinic chlorocarbon selected from the group consisting of 1,1,3,3-tetrachloropropene and 1,3,3,3-tetrachloropropene by a. admixing one mole of a hydrocarbon compound selected from the group consisting of propene, 1-chloropropene, 3-chloropropene, 1,1-dichloropropene, 1,3-dichloropropene, 3,3,-dichloropropene, 1,1-dichloropropane, 1,2-dichloropropane, 1,3-dichloropropane, 1,1,3-trichloropropene, 1,3,3-trichloropropene, 3,3,3-trichloropropene, and mixtures thereof with from about three to about four moles of an inert diluent at about 300° C. to about 400° C. to form a mixture of said hydrocarbon compound with said gas;

b. mixing said admixture with chlorine gas;

c. thermally treating the mixture of step b. at a temperature of from about 480 ° C. to about 520° C.; and d. separating said olefinic chlorocarbon.

* * * * *